US007545913B2

(12) United States Patent
Connelly et al.

(10) Patent No.: US 7,545,913 B2
(45) Date of Patent: Jun. 9, 2009

(54) INTEGRATED DIGITAL SENSOR AND X-RAY TUBE USED WITH A PASS-THROUGH

(75) Inventors: Jack Connelly, Camillus, NY (US); Frank Rapa, Manhasset Hills, NY (US); Stan Mandelkern, Teaneck, NJ (US)

(73) Assignee: Schick Technologies, Inc., Long Island City, NY (US)

( * ) Notice: Subject to any disclaimer, the term of this patent is extended or adjusted under 35 U.S.C. 154(b) by 0 days.

(21) Appl. No.: 11/617,944

(22) Filed: Dec. 29, 2006

(65) Prior Publication Data
US 2008/0159483 A1 Jul. 3, 2008

(51) Int. Cl.
*H05G 1/64* (2006.01)
*H05G 1/28* (2006.01)
*G01D 18/00* (2006.01)

(52) U.S. Cl. .......................... 378/98; 378/162; 378/207

(58) Field of Classification Search ................ 378/114, 378/162, 165, 196, 197, 98, 98.8, 207
See application file for complete search history.

(56) References Cited

U.S. PATENT DOCUMENTS

| 3,922,788 | A | 12/1975 | Rota | 32/22 |
|---|---|---|---|---|
| 4,332,557 | A | 6/1982 | Watanabe | 433/77 |
| 6,134,298 | A | 10/2000 | Schick et al. | 378/98.8 |
| 6,666,579 | B2 * | 12/2003 | Jensen | 378/197 |
| 2002/0067407 | A1 | 6/2002 | Cooper | 348/66 |
| 2003/0232305 | A1 | 12/2003 | Warner | 433/98 |
| 2004/0082849 | A1 * | 4/2004 | Schweikard et al. | 600/424 |
| 2005/0211908 | A1 | 9/2005 | Dieras et al. | 250/370.09 |
| 2005/0254625 | A1 | 11/2005 | Schick et al. | 378/98 |
| 2006/0152513 | A1 * | 7/2006 | Saito | 345/501 |
| 2007/0223816 | A1 * | 9/2007 | Horovitz et al. | 382/181 |

* cited by examiner

*Primary Examiner*—Irakli Kiknadze
(74) *Attorney, Agent, or Firm*—Fitzpatrick, Cella, Harper & Scinto

(57) ABSTRACT

A method of operating a digital x-ray system having a plurality of information processors, each information processor associated with a corresponding one of a plurality of operatories. The method includes detecting at least one image in response to at least one energy source emitting energy, while the energy source is associated with an extension arm which is positioned to serve a selected one of the operatories, and outputting an electrical image data signal representing the detected image. The method also includes detecting a position of the extension arm, and automatically routing the outputted electrical image data signal to the information processor associated with the selected operatory based on the detected position.

20 Claims, 7 Drawing Sheets

INTEGRATED DIGITAL SENSOR AND X-RAY TUBE USED WITH A PASS-THROUGH

BACKGROUND OF THE INVENTION

1. Field of the Invention

The present invention generally relates to the field of digital radiography systems, and more particularly to a digital radiography station that can be shared among operatories, each having a dedicated computer, in which image data is automatically routed to the appropriate dedicated computer depending on which operatory is being served by the digital radiography station.

2. Related Art

X-ray radiation has long been employed in the fields of medicine and dentistry to capture images of the human anatomy. Physicians, dentists, and oral surgeons typically use these images to aid in the diagnosis and treatment of conditions and disease, and in the case of dentists and oral surgeons in particular, images of a patient's teeth, mouth, and gums are critical for such purposes.

The most conventional x-ray imaging technique uses radiographic film as the imaging receptor. According to such a technique, a cartridge containing a piece of photographic film is placed in the patient's mouth, for example behind a patient's teeth, and an x-ray beam is projected through the teeth and onto the film. After the film is exposed in this manner, it is developed in a dark room or a closed processor using special chemicals to obtain a photographic image of the tooth.

Solid-state sensors which convert x-rays into an electrical signal have increasingly begun to be used in place of photographic film. Such electronic sensors may include a charge-coupled device (CCD), an active pixel sensor (APS) array, or another type of filmless radiation sensor.

Such digital dental radiography systems offer many advantages over traditional film-based radiography systems. For example, an x-ray sensor is typically more sensitive to x-rays than is film, thereby allowing the x-ray dosage to the patient to be significantly lowered, sometimes by as much as 90% or more. Furthermore, images of the anatomy may be generated by a computer almost instantaneously, thus improving workflow and eliminating the entire film development process, including the use of potentially harmful chemicals. Moreover, because the images are generated electronically, they can be easily stored in and accessed from a computer database.

In digital radiography, the signal from the electronic sensor can be transmitted to the computer or other output device via a long, flexible cable. In other systems, a wireless interface may be used in place of the cable, such that signals are transmitted from the electronic sensor to the computer or output device via a radio-frequency waveform. Wireless communications systems have made inroads into many disciplines and may be preferable in medical and dental digital imaging for a number of reasons. For example, extra wires can be inconvenient for the patient and clinician. Also, in certain diagnostic procedures, the sensor wires may be cumbersome and could limit placement of the sensor with respect to the x-ray tube and computer. In digital dental radiography in particular, such wires can limit sensor placement in the mouth. Furthermore, mechanical failure of the wire can occur due to strain. A wire can also create a trip hazard.

In digital x-ray imaging, the energy source (e.g., the x-ray generator) is typically configured to provide the radiation directly towards the image detector, which is often distant from the source and/or from computer processor components. As discussed above, the image data is often conveyed from the detector using a cable, and in certain applications this cable can be inconvenient for the patient and the operator as it may present various electrical and mechanical constraints. A wireless system, on the other hand, can provide a wider range of degrees of freedom of the detector with respect to the source.

More particularly, in digital dental x-ray imaging, an electronic sensor is placed in the patient's mouth behind the teeth to be examined, and an x-ray beam is projected from an energy source towards the electronic sensor and through the patient's teeth. The x-rays impinge on the electronic sensor, which converts the x-rays into an electrical signal. The electrical signal can be transmitted over a wire to a computer, as described above, and the computer then processes the signal to produce an image on an associated output device such as a monitor or printer. Alternatively, the electrical signal could be transmitted wirelessly from the electronic sensor to a receiver which in turn delivers the signal to the computer.

Communication between the sensor and computer can be effected in various ways. One way is through a commonly available and accessible digital port such as, but not limited to, the Universal Serial Bus (USB). The USB is a serial channel of up to 480 megabits per second (Mpbs) that can be used for peripherals. The USB is a token-based bus; that is, the USB host controller broadcasts tokens on the bus and a device that detects a match on the address in the token responds by either accepting or sending data to the host. The host also manages USB bus power by supporting suspend/resume operations. The USB is advantageous in that it does not require the use of specially designed hardware inside the computer; once the appropriate software has been installed, a peripheral can be plugged into the USB port. In addition, one device can be unplugged and another plugged in without changing the hardware configuration of the computer.

A computer's Peripheral Component Interconnect (PCI) bus and Industry Standard Architecture (ISA) bus also provide a data path between the electronic sensor and the computer's Central Processing Unit (CPU). The PCI bus is an internal 32-bit local bus that runs at 33 MHz and carries data at up to 133 megabytes per second (Mbps), while the ISA bus is an 8- or 16-bit internal bus that carries data at up to 8.33 Mbps. Each of these buses may act as an interface between the sensor and the computer.

A filmless dental radiography system using a USB port, along with an exemplary intra-oral detector, is described in U.S. Pat. No. 6,134,298 to Schick et al., which is hereby incorporated by reference. In Schick et al., the intra-oral detector outputs image data which is received by a computer through its USB port. The system comprises an electronic sensor 1 with connector 1a, a remote board 2 containing the necessary processing circuitry, and a computer 4, the sensor 1 being connected through the computer's USB port. While Schick et al. is well suited for its intended purposes, the interface may not be convenient for certain clinical environments, for reasons that will become apparent.

Dental operatories are often laid out adjacent to each other, and are often configured to share capital equipment in an effort to save cost, among other reasons. For instance, the dental x-ray tube is not typically in continuous use during a patient visit and, as discussed in U.S. Pat. No. 3,922,788 to Rota for example, it may be more cost-effective to share the device between adjacent operatories by moving the device through an opening or pass-through between the operatories. U.S. Pat. No. 4,332,557 to Watanabe, as another example, discusses mounting an x-ray unit such that it may be pivoted and serve adjacent operatories.

The personal computer has become an increasingly important piece of capital equipment in a dental office. It is called upon to serve a variety of tasks, including scheduling and billing as well as patient education, and can form the basis for driving, analyzing, and sharing data from other capital equipment such as digital imaging sensors. The diversity of these tasks often demands that a computer be placed within each and every dental operatory. For instance, while a patient sits in the dental chair, the computer may be used by the practitioner to enter office notes and clinical findings, or as a teaching tool to explain treatment. It can be impractical to share a single computer among the operatories since a particular computer might be in use for a particular patient—for example, might have a patient file open—and switching between patient files can be tedious.

Therefore, while an x-ray tube and digital sensor may be shared among two operatories, it is not as likely that a computer could efficiently be used as a shared resource. As such, the installation of a digital imaging system may require a convenient means of conveying data from a single digital sensor to two separate computers. In a typical installation such as that disclosed in Schick et al, however, the sensor would need to be disconnected from one computer, hand carried to the other, and then reconnected to the second computer. This process can not only be cumbersome, but can also place significant strain upon the electronics interface and computer connectors, which in turn can lead to product failures.

Generally, digital dental imaging detectors operate separate from and asynchronous to the x-ray detector source. Recently, however, detector wiring and circuitry have been integrated with an x-ray source. Such is the case with U.S. Patent Application Publication No. US 2005/0254625 A1 to Schick et al., which is hereby incorporated by reference in its entirety, as if fully set forth herein. There are several advantages to this approach. First, there are fewer components and wires to interfere with the patient and clinician. Furthermore, if a wireless dental sensor is utilized, the radiofrequency receiver can be integrated in close proximity to the patient and in a practical and convenient location, such as inside the x-ray collimator. Moreover, the x-ray trigger signal can be utilized to initiate sensor acquisition.

While this solution is robust, a pass-through configuration, in which an x-ray tube is pivotable through a pass-through so as to allow the device to intermittently serve multiple operatories, still requires a mechanism for automatically conveying the image data from the processing circuitry to the appropriate target computer. Conventional approaches to this problem are unsatisfactory. For example, one standard approach is to use a mechanical A/B switch, in which the practitioner moves the A/B switch into position based on which computer is being used for which operatory. However, mechanical A/B switches are clumsy, aesthetically unpleasing, require manual operation by the practitioner as described, and can be difficult to install seamlessly within a dental or doctor's office.

Given the foregoing, what is needed is a system and method which overcomes the above-mentioned problems and provides a digital x-ray system, shared in a pass-through configuration, which can automatically route image data from the shared digital x-ray system to the appropriate operatory computer.

SUMMARY OF THE INVENTION

The present invention meets the above-identified needs by providing, in at least one embodiment, a system, method, and apparatus for integrating a digital sensor and x-ray tube, shared in a pass-through configuration with dedicated operatory computers, which can automatically route image data from the shared digital x-ray system to the appropriate operatory computer depending on the position of the x-ray arm. Mechanical motion of the extension arm from one operatory to another, as the arm swings from one side of the partition to another, actuates the direction of data conveyance.

An advantage of the invention is that it can ensure that image data from the shared digital x-ray system is automatically routed to the appropriate or target dedicated computer, thereby reducing or eliminating the need for a practitioner to control routing of the image data by way of manual operation. Another advantage of the present invention is that it can provide a seamless, easy-to-use installation of a digital radiographic system. The system includes an x-ray source and a digital sensor that can be easily shared in side-by-side or multiple operatories.

The present invention in accordance with one embodiment provides a method of operating a digital x-ray system having a plurality of information processors, each information processor associated with a corresponding one of a plurality of operatories. The method includes detecting at least one image in response to at least one energy source emitting energy, while the energy source is associated with an extension arm which is positioned to serve a selected one of the operatories, and outputting an electrical image data signal representing the detected image. The method also includes detecting a position of the extension arm, and automatically routing the outputted electrical image data signal to the information processor associated with the selected operatory based on the detected position.

The method may further include transmitting a signal generated based on the detected position to an Ethernet controller which performs the routing step. The method may further include transmitting a signal generated based on the detected position to a latching relay which performs the routing step. The method may further include indicating the detected position to an operator. The step of detecting a position of the extension arm may include using a Hall effect switch or a micro-switch.

The present invention in accordance with another embodiment provides a digital x-ray system having a plurality of information processors, each information processor associated with a corresponding one of a plurality of operatories. An electronic sensor is adapted to detect at least one image in response to at least one energy source emitting energy, while the energy source is associated with an extension arm which is positioned to serve a selected one of the operatories, and is adapted to output an electrical image data signal representing the detected image. A detector is adapted to detect a position of the extension arm, and a controller is adapted to automatically route the outputted electrical image data signal to the information processor associated with the selected operatory based on the detected position.

The detector may comprise a Hall effect switch or a micro-switch. The detector may comprise a photodetector which detects light emitted from a user-perceptible interface based on a position of the extension arm, and the system may comprise an interference material which blocks the emitted light from being detected by the photodetector when the extension arm is in one position and does not block the emitted light from being detected by the photodetector when the extension arm is in another position. The interference material may comprise one of plastic and metal. The user-perceptible interface may comprise a plurality of LEDs.

The controller may be an Ethernet controller or a latching relay. The system may further comprise a user-perceptible interface for indicating the detected position to an operator, and the user-perceptible interface may comprise a plurality of LEDs. The electronic sensor may be a wireless sensor or a wired sensor.

The present invention in accordance with another embodiment provides a method comprising the steps of detecting a position of an extension arm electronically, and forwarding an electrical image data signal to one of a plurality of information processors based on the detected position.

Further features and advantages of the present invention as well as the structure and operation of various embodiments of the present invention are described in detail below with reference to the accompanying drawings.

BRIEF DESCRIPTION OF THE DRAWINGS

The features and advantages of the present invention will become more apparent from the detailed description set forth below when taken in conjunction with the drawings in which like reference numbers indicate identical or functionally similar elements.

DETAILED DESCRIPTION

The present invention in one exemplary embodiment provides a digital radiology system that can be shared among two or more dental operatories, each operatory having a dedicated computer. An x-ray system according to an exemplary embodiment of the invention includes integrated support for digital intraoral sensors and a computer interface used to provide signals between a sensor and an appropriate dedicated computer running acquisition and image processing. The present invention according to an exemplary embodiment allows sharing of an x-ray device among more than one operatory by automatically routing the computer interface signals to the appropriate operatory computer depending on the position of an x-ray generator arm.

Figure 1:
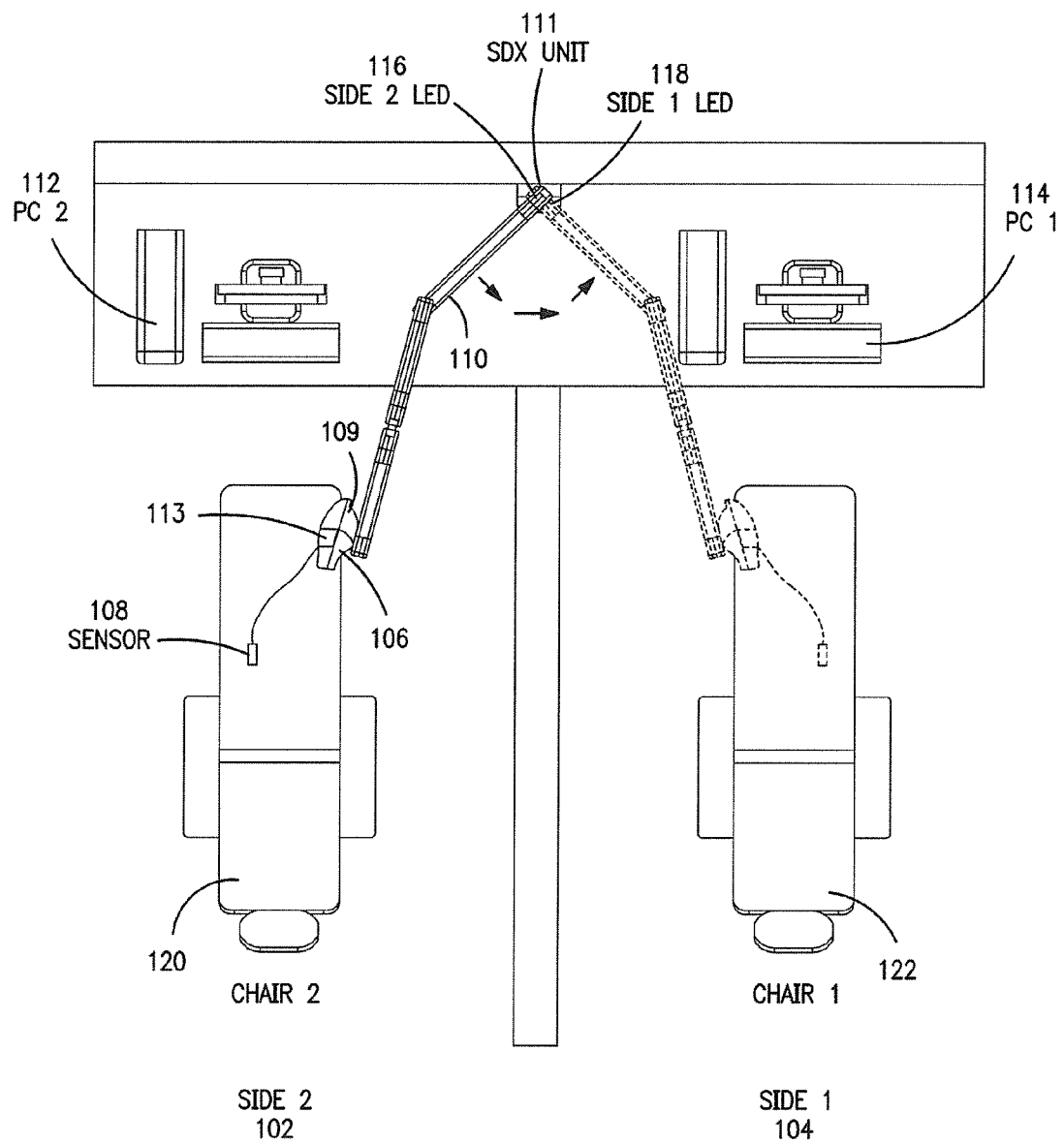
FIG. 1 is a diagram showing an exemplary environment that is suitable for practicing the present invention.

FIG. 1 is a diagram showing an exemplary environment in which the present invention, in a preferred embodiment, can be implemented. In FIG. 1, an example of a physical setup of a system 100 is shown, in which side-by-side operatories 102, 104 are served by and conveniently share an x-ray source 106 and a digital sensor 108, the x-ray source 106 being located at an end of an extension arm 110. The x-ray source 106 is housed in an x-ray tube enclosure 109, and the x-ray tube enclosure 109 and the extension arm 110 rotate between the operatories 102, 104 to serve each operatory. For this purpose, the extension arm 110 is pivotally attached to and controlled by a timer or control box 111 of the x-ray system. As shown in FIG. 1 by the faded lines, the extension arm 110 can be pivoted from operatory 102 to operatory 104 (and vice versa). Each operatory 102, 104 has, for example, a chair 120, 122, respectively, and, of course, may have its own cabinetry and associated devices (lamps, sinks, etc.), although in other embodiments other types of operatory arrangements may be employed instead.

Dedicated computers 112 and 114 correspond to operatories 102 and 104, respectively, and, among other functions and uses, receive and process image data from the digital sensor 108. The computers 1112, 114 may be any information processor or conventional desktop, tower, laptop, notebook computer, personal computer, handheld device, palm device, server platform or other information appliance platform that is equipped with an interface such as a USB port and a corresponding USB channel, or another suitable interface/channel for communicating with sensor 108. In addition to the USB port, each computer 112, 114 is equipped with various known software modules that support the USB channel, such as USB host controller software, and a known USB hardware interface. Preferably, each computer 112, 114 stores and/or otherwise operates in accordance with programs or routines for implementing the method of this invention to be described below in conjunction with FIG. 4. The programs and routines can be stored on a memory that is readable by the respective computers 112, 114. That memory also is referred to herein as a storage device (as described below). Each computer 112, 114 is either connected to or has built in one or more input devices, such as, for example, a keyboard and a mouse, and one or more output devices, such as a monitor and a printer. These devices allow the user to control the operation of the system 100, and to view dental images that the system creates. Computers 112, 114 may also include or be connected to some type of storage device (not shown), such as a hard drive, for permanent storage of the images in patient files. Of course, the present invention is not limited for use only with the types of computers and input and output devices referred to herein, and, in other embodiments, other suitable types of information processors and user interfaces also may be employed.

An electronic device (not shown in FIG. 1 and to be described in more detail later) is also provided for detecting the direction in which the extension arm 110 is facing. Once this position is detected, image data can be automatically routed from the digital sensor 108 to the appropriate dedicated computer 112, 114. LEDs 116, 118 for each side, respectively, enable an operator to visually confirm, based on which LEDs 116, 118 are lit, the position that is detected and the operatory computer that is receiving the image data. By allowing the operator to confirm the computer port that is active, the operator can troubleshoot the system 100. This provides feedback to the operator to enable unintended errors to be avoided.

The x-ray source 106 may be of any standard type. In the dental field, for example, an x-ray source used for intra-oral examinations is well known to those having ordinary skill in the art. Typically, the source emits 65-75 kVp of energy with a tube current of 4-10 mA. The duration of exposure varies depending upon patient size and the area being imaged. The x-ray tube enclosure 109 may house processing circuitry necessary to, among other things, effect x-ray signal integration by the electronic sensor 108 and read-out image data from the electronic sensor 108. The enclosure 109 may also include a wireless receiver as is described and shown in U.S.

Patent Application Publication No. US 2005/0254625 A1 to Schick et al., which was incorporated by reference above (see, e.g., FIG. 1 of Schick et al.). FIG. 1 of the present application shows an example of a suitable placement for a wireless receiver 113, which in this example is located on the enclosure 109; of course, there are other suitable locations as explained herein.

In operation according to the embodiment of FIG. 1, the digital sensor 108 is placed behind the anatomy being examined, for example, a patient's teeth. The x-ray source 106 emits x-rays which pass through the anatomy and impinge on the digital sensor 108, which converts the x-rays either directly or indirectly to an array of charge or an electric signal representing a radiographic image. The digital sensor 108 itself may utilize any of a number of detector technologies, such as CCD, CMOS-APS, TFT (Thin-film-transistor) arrays, etc., and may comprise any solid state device capable of converting electromagnetic radiation into electrical signals.

The digital sensor 108 can communicate with the x-ray source 106 via either a wired or a wireless transmission protocol. A wired sensor may interface through a connector located (for example) inside the chassis surrounding the x-ray tube, while a wireless sensor may communicate with a wireless receiver housed within the x-ray collimator, x-ray tube enclosure, or any other suitable location, such as on an outside of the x-ray tube enclosure, as shown in U.S. Patent Application Publication No. US 2005/0254625 A1, which has been incorporated by reference herein. Of course, the invention is not limited to these examples, In any case, the electric signal derived by the digital sensor 108 is ultimately delivered to an appropriate one of the dedicated computers 112, 114 depending on the position of the extension arm, in accordance with the present invention, as will be further described below.

In one embodiment each computer 112, 114 communicates with the sensor 108 via a wired/wireless interface such as described above, cabling within the extension arm 110, and electronics (all not shown) embedded within the x-ray system 100. Each computer 112, 114 can drive the sensor 108 and acquire data from a particular patient via the sensor 108, among other functions. Each computer 112, 114 performs image processing functions by processing the received signals to produce an image on an associated output device such as a monitor or printer. The computer can also perform other ancillary roles such as scheduling and billing, as well as providing patient education. Of course, the computer may also drive other hardware within the dental operatory.

Figure 2:
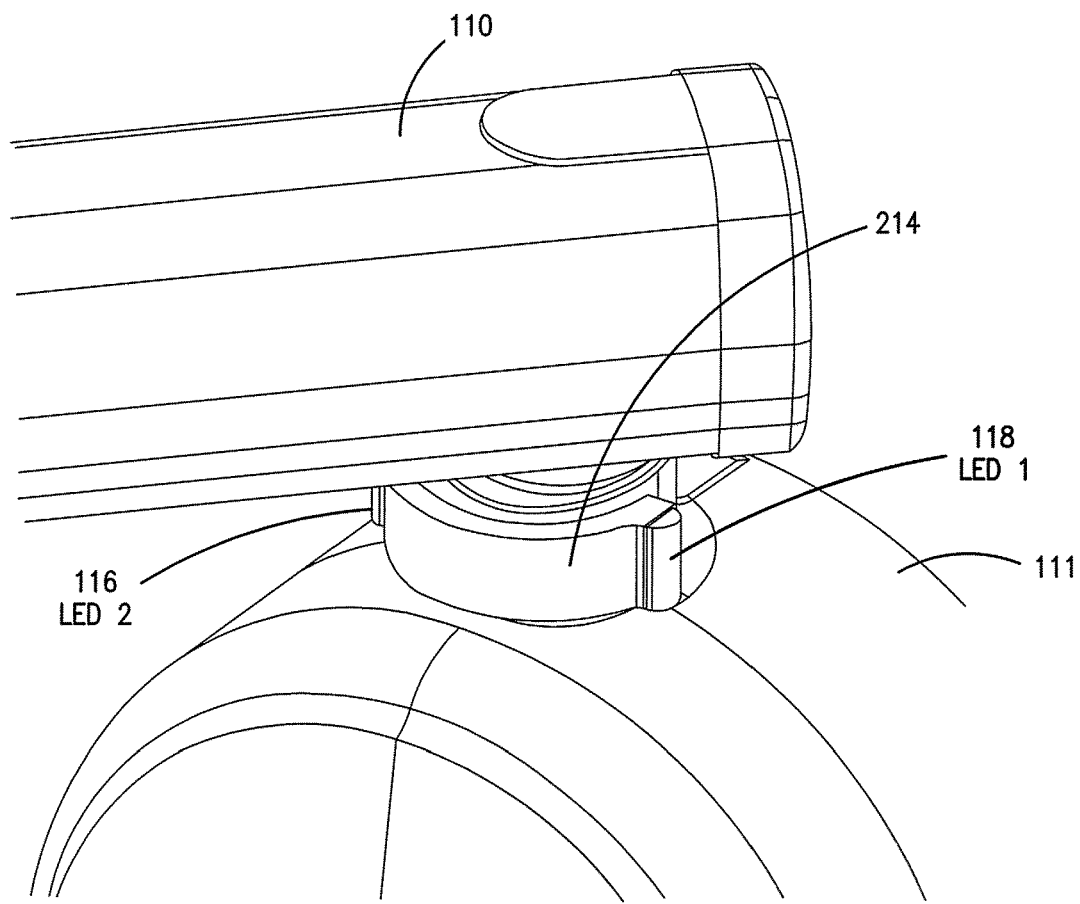
FIG. 2 is a close-up view of the pivot point of an extension arm of a digital x-ray system according to one embodiment of the present invention.

The x-ray source 106 is mounted on the extension arm 110 and rotated from one side to the other using a pass-through or other configuration so that the x-ray source can be easily used for either operatory 102, 104 by a clinician on a patient. The present invention, according to at least one exemplary embodiment, allows sharing of an x-ray system 100 among each operatory 102, 104 by automatically routing the computer interface signals to the appropriate computer 112, 114 depending on the position of the extension arm 110, as further described below. FIG. 2 is a close-up view of the pivot point of the extension arm 110. The extension arm 110 is attached to a timer box post 214 which rotates through the timer box 111, thereby enabling the extension arm 110 to pivot with respect to the timer box 111. Of course, the invention is not limited to the example shown.

Figure 3:
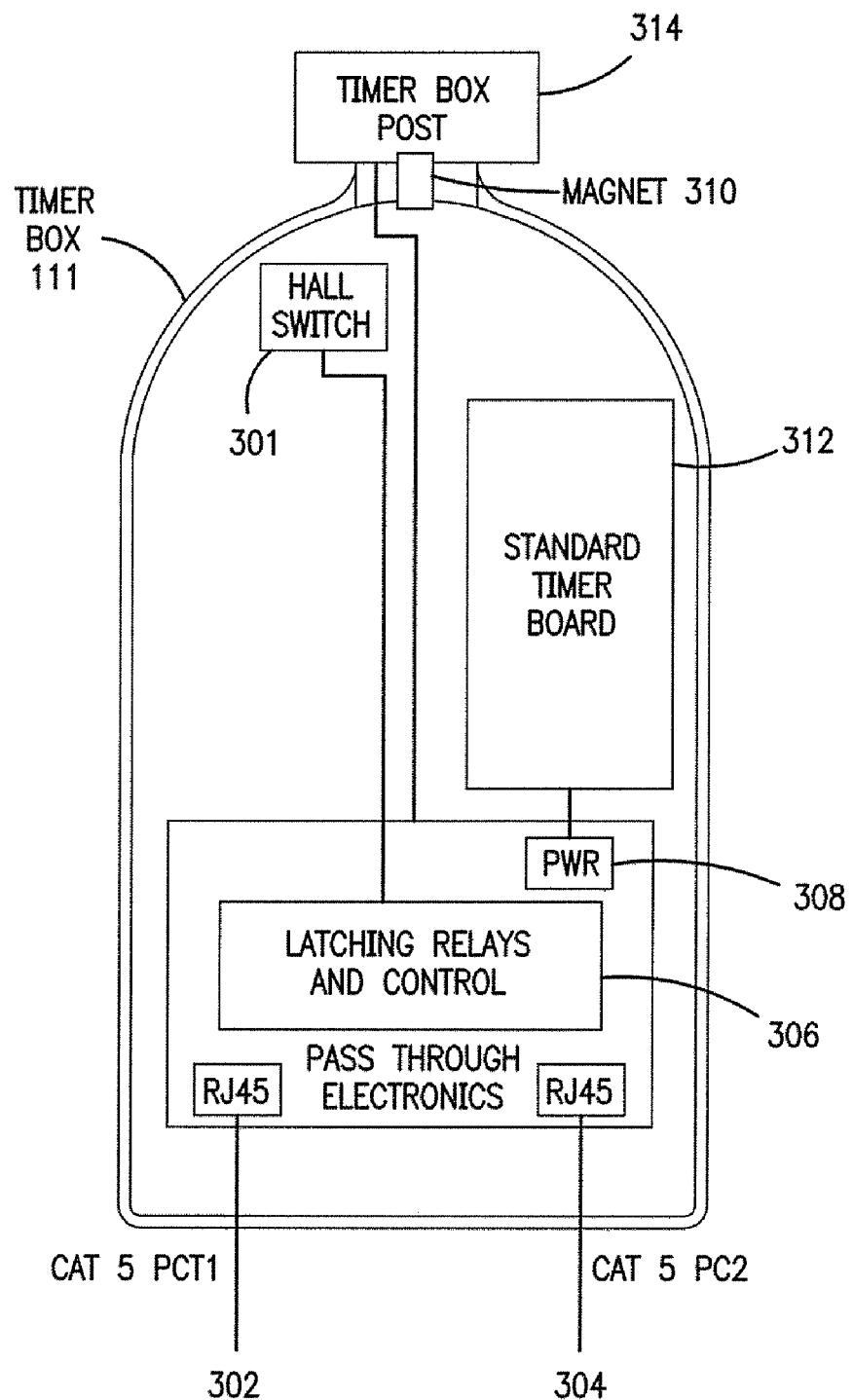
FIG. 3 shows one embodiment of the invention, in which orientation of the extension arm is detected using a Hall-effect switch.

FIG. 3 shows one exemplary embodiment of the invention, in which orientation of the extension arm 110 (not shown in FIG. 3) is detected using a solid state device such as a Hall-effect switch 301 in conjunction with a magnetic field located at or near the pivot point. In this embodiment, the magnetic field is provided by a ferrite rod or magnet 310 which is located on and rotates with the timer box post 314 with respect to the timer box 111. The timer box 111 includes cables 302, 304, latching relay driver 306, power supply 308, a standard timer board 312 for controlling the technique factors of the x-ray system (such as the amount of x-ray energy and the duration of exposure and the like), and the Hall-effect switch 301 located at or within the timer box 111.

The timer box 111 can include software control programs and operating routines stored in an associated memory or memories located within the timer box 111, for example within standard timer board 312 or at any other suitable location, for implementing the present invention. Various memories can also be located within the timer box 111, for example within the standard timer board 312 or at any other suitable location, for receiving and storing image data before the image data is transferred to the appropriate dedicated computer.

In this way, FIG. 3 shows an implementation for routing data from the x-ray source 106 to the appropriate operatory computer 112, 114 in accordance with one embodiment of the present invention. It is of course to be understood that various modifications can be made to the embodiment shown herein. For example, the magnet 310 and the Hall-effect switch 301 can be placed at any suitable location and are not limited to only those locations shown in FIG. 3.

An electrical signal representing the detected image data is sent from the digital sensor 108 that detected the image through a wired interface or is transmitted from the digital sensor 108 to a wireless interface. The wired or wireless interface then conveys the data through, for example, one or more cables running along the extension arm 110 (or through another wireless interface) to, e.g. a memory (not shown) of, for example, a standard timer board 312 located in the timer box 111, after which it is delivered to the appropriate dedicated computer according to the detected position. Of course, the memory may be located in a place other than the standard timer board 312, for example elsewhere in the timer box 111; alternatively, the data may pass through the timer box 111 without being stored in a memory. In any event the timer box 111 is connected to and controls the x-ray source 106 and the extension arm 110, and the operator uses the timer box 111 to perform such functions as setting the duration of exposure, setting other parameters, etc.

In this embodiment, the magnet 310 rotates with the rotation of the extension arm 110 and the timer box post 314, while the Hall-effect switch 301 remains stationary. As is well known in the art, a Hall-effect switch makes use of a phenomenon observed in thin strips of metal and in some semiconductors: i.e., when a strip carrying electrical current longitudinally is placed in a magnetic field that is perpendicular to the strip's plane, a voltage appears between opposite edges of the strip that forces a current through an external circuit.

In this embodiment, as the x-ray tube 106 moves from one operatory to another, being maneuvered by an operator, for example, thus rotating the extension arm 110 on a pivot, the magnetic field provided by the magnet 310 changes relative to the Hall-effect switch 301, and the position of the extension arm 110 is thereby detected by the Hall-effect switch 301. Specifically, when the rotation of the extension arm 110 is such that the magnetic field provided by the magnet 310 becomes perpendicular to the Hall-effect switch 301, a voltage appears across the Hall-effect switch 301. If there is a voltage across the Hall-effect switch 301, it means that one predetermined position is detected, and if there is no voltage across the Hall-effect switch 301, it means that another predetermined position is detected.

In more detail the Hall-effect switch 301 sends a signal, for example, a high or low signal, based on the voltage and in effect indicating the detected position of the extension arm 110, to a latching relay 306. The system can be set up, for example, such that when a high signal is received from the Hall-effect switch 301, the image data is conveyed by the latching relay 306 to one computer, and when a low signal is received from the Hall-effect switch 301, the image data is conveyed by the latching relay 306 to another computer. In this way, the latching relay 306 actuates image data transfer, for example from a memory located in the timer box 111, to the appropriate dedicated computer. This data transfer can occur through a wired interface or through a wireless interface.

A latching relay is an electromechanical relay that locks into whichever mode it is energized for. In this exemplary embodiment, the latching relay 306, based on the signal from the Hall-effect switch 301, acts as a controller when actuated in that it effects the flow of data transfer from the timer box 111 to either a first or a second USB interface (or other suitable) module in computer 112 or 114, respectively, depending on the detected position indicated by the signal. The data transfer can be via a corresponding CAT5 cable 302, 304 or via another suitable type of interface, whether wired or wireless; while CAT5 cables with eight conductors are utilized in this embodiment, the invention is of course not limited thereto.

The local power supply 308 draws current from the timer box 111 which is then provided to the latching relay driver 306 through multiplexing electronics (not shown). The latching relay 306 is preferred for use in this invention as it only requires minimal power for operation, is bidirectional, switches the variety of voltages present on the CAT5 cable without additional level shifting, and is immune to damage from electrostatic discharge.

Of course, the invention is not limited to using a latching relay 306. Other technologies, switches, and/or interfaces can be used instead to actuate data transfer to the appropriate dedicated computer. For example, the Hall-effect switch 301 can deliver the signal indicating the detected position to an Ethernet controller, which effects the flow of data transfer to an Ethernet or Internet Protocol (IP) address of the appropriate computer. Technologies such as Bluetooth or A02.11 networks also can be used.

A Hall-effect switch that can be used with the present invention is, for example, model OHB900, manufactured by TT Electronics OPTEK Technology. Of course, any suitable Hall-effect switch can be used.

Figure 4:
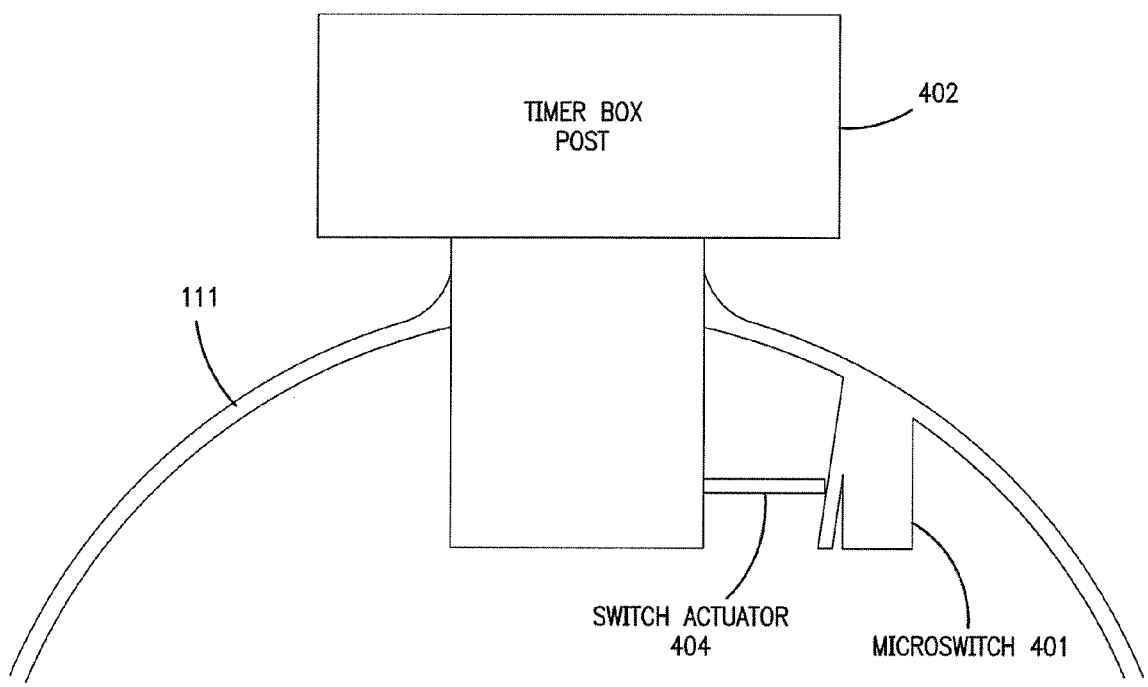
FIG. 4 shows another embodiment of the invention, in which orientation of the extension arm is detected using a micro-switch.

FIG. 4 shows another embodiment of the invention, in which orientation of the extension arm 110 (not shown in FIG. 4) is detected using a micro-switch 401 located on or mounted to or in the timer box 111, or at any other suitable location. FIG. 4, then, illustrates an implementation of routing data from the x-ray source 106 to the appropriate operatory computer 112, 114 in accordance with another embodiment of the present invention. It is noted that this embodiment can operate in conjunction with components similar to the cables 302, 304, latching relay driver 306, power supply 308, and standard timer board 312 shown in FIG. 3, although such components are not shown in FIG. 4 for simplicity sake. For example, the micro-switch 401 can be connected to the latching relay 306, with the other connections similar to those shown in FIG. 3.

An electrical signal representing image data detected by sensor 108 is sent from the digital sensor 108 through a wired interface or is transmitted from the digital sensor 108 through a wireless interface. The wired or wireless interface then conveys the data through one or more cables running, for example, along the extension arm 110 (or through another wireless interface) to a circuit board located in the timer box 111. The timer box 111 is connected to and controls the x-ray source 106 and the extension arm 110, and the operator uses the timer box 111 to perform such functions as setting the duration and strength of exposure, setting other parameters, etc. The timer box post 402 rotates through, and relative to, the timer box 111.

Micro-switches are electric switches which are activated by the physical motion of mechanical devices. In this embodiment, the micro-switch 401 is activated by the physical motion of the switch actuator 404 located on the timer box post 402. The micro-switch 401 offers a zero impedance when it is closed (i.e. by contact of the switch actuator 404), and an infinite impedance when it is open (i.e. no contact with the switch actuator 404). In operation, the x-ray source 106 moves from one operatory to another, being maneuvered by an operator for example, thus rotating the extension arm 110 on a pivot, and thereby rotating the timer box post 402 and therefore the switch actuator 404 located thereon. When the timer box post 402 rotates far enough in one direction in one operatory, the switch actuator will make contact with the micro-switch 401. Thus, the switch actuator 404 is in contact with the micro-switch 401 when the extension arm 110 is moved into one position, and is not in contact with the micro-switch 401 when the extension arm 110 is moved into another position (another operatory). In this way, the micro-switch 401 offers either a zero impedance (closed) or an infinite impedance (open) depending upon the position of the extension arm 111 (i.e. depending on which operatory the arm 110 is placed in). When the rotation of the extension arm 110 is such that the micro-switch 401 offers a zero impedance, it means that one position of the extension arm 110 is detected, and when the rotation is such that the micro-switch 401 offers an infinite impedance, it means that another position is detected.

In more detail, the micro-switch 401 sends a signal, for example a high or low signal, based on the impedance and in effect indicating the detected position of the extension arm 110, to a latching relay (e.g. 306). The system can be set up, for example, such that when a signal is received from the micro-switch 401 indicating a zero impedance, the image data is conveyed by the latching relay (e.g. 306) to one computer, and when a signal is received from the micro-switch 401 indicating an infinite impedance, the image data is conveyed by the latching relay (e.g. 306) to another computer. In this way, the latching relay (e.g. 306) actuates data transfer to the appropriate dedicated computer. That is, the latching relay (e.g. 306), based on the signal from the micro-switch 401, effects the flow of image data transfer from the timer box 111 to either a first or a second USB interface (or other suitable) module in computer 112 or 114, depending on the detected position, as in the case of FIG. 3.

The image data transfer can be via a corresponding CAT5 cable or via another suitable type of interface, whether wired or wireless. While CAT5 cables with eight conductors are utilized in this embodiment, the invention is of course not limited thereto. The local power supply draws current from the timer box 111 which is then provided to the latching relay driver through multiplexing electronics (not shown).

Of course, this embodiment is not limited to using a latching relay driver. Other technologies and interfaces can be used instead to actuate data transfer to the appropriate dedicated computer. For example, the micro-switch 401 can deliver the signal indicating the detected position to an Ethernet controller, which effects the flow of data transfer to an Ethernet or Internet Protocol (IP) address of the appropriate computer. Technologies such as Bluetooth or A02.11 networks can also be used.

A micro-effect switch 401 that can be used with the present invention is, for example, model E61-10k manufactured by Cherry. Of course, any other suitable micro-effect switch can be used instead.

The switch actuator 404 can be, for example, a piece of metal or any other suitable material, and can be of any suitable shape. As described herein, the switch actuator 404 rotating on the timer box post 412 makes contact with the micro-switch 401 to close the micro-switch 401 while the extension arm 110 is facing one operatory; when the extension arm 110 is facing another operatory, the micro-switch 401 is open.

Figure 5:
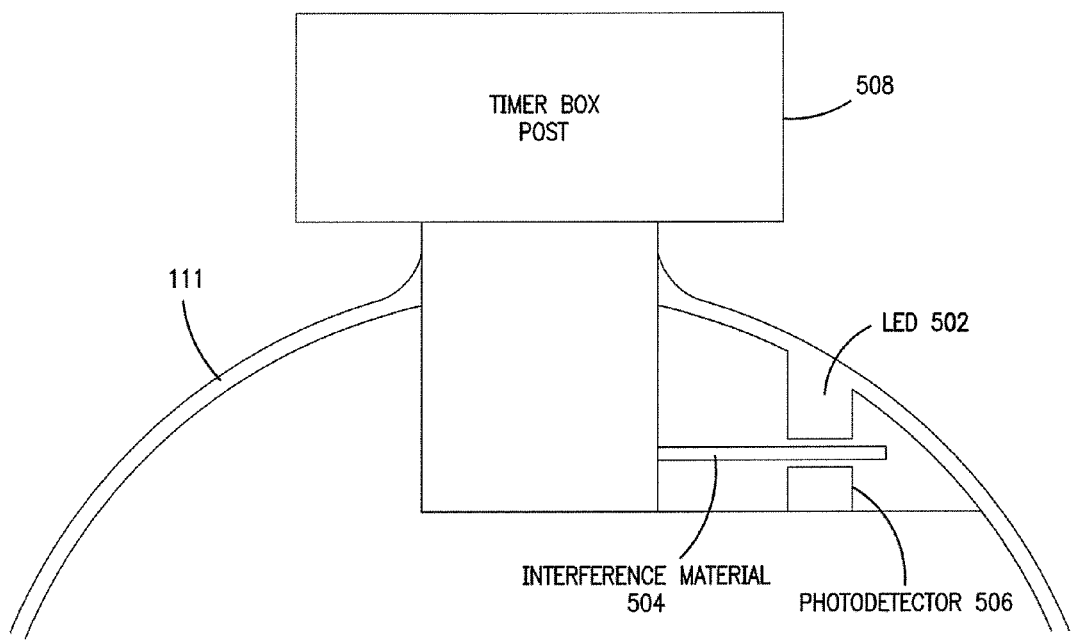
FIG. 5 shows another embodiment of the invention, in which orientation of the extension arm is detected using an electro-optic sensor.

FIG. 5 shows another exemplary embodiment of the invention, in which orientation of the extension arm is detected using an electro-optic sensor. It is noted that this embodiment can operate in conjunction with components similar to the cables 302, 304, latching relay driver 306, power supply 308, and standard timer board 312 shown in FIG. 3, although such components are not shown in FIG. 5 for simplicity sake. For example, the photodetector 506 can be connected to the latching relay 306, with the other connections similar to those shown in FIG. 3.

In FIG. 5, the timer box post 508 rotates through, and relative to, the timer box 111, thereby enabling the extension arm 110 attached thereto (not shown in FIG. 5) to pivot with respect to the timer box 111. An LED 502 is mounted at the timer box 111, and does not rotate. An interference material 504 is mounted on (or otherwise coupled to), and rotates with, timer box post 508; the interference material 504 is preferably mounted below the LED 502. A photodetector 506 is mounted at the timer box 111, but below the plane of the interference material 504, and does not rotate. The interference material 504 can be any suitable material that blocks light, for example plastic or metal, and can be of any suitable shape. It is of course to be understood that the interference material 504 is not limited to these examples. It is also to be understood that modifications may be made to the positioning of the LED 502, interference material 504, and photodetector 506; for example, the positions of the LED 502 and the photodetector 506 could be altered or swapped.

In the embodiment of FIG. 5, the LED 502 emits light which is registered by the photodetector 506 when the light is not being blocked by the interference material 504. Because the interference material 504 moves with rotation of the timer box post 508, which rotates as the extension arm 110 (not shown in FIG. 5) pivots, the interference material 504 will either block or not block the light depending on the position of the extension arm 110. In this way, the LED 502 emits light which is registered by the photodetector 506 when the extension arm 110 is in one operatory, and the light is not registered by the photodetector 506 when the extension arm 110 is in another operatory. The photodetector 506 sends a signal, for example a binary or other signal, depending on whether the light from the LED 502 is being registered, to a latching relay (e.g. 306) which actuates data transfer to the appropriate dedicated computer depending on which operatory is indicated by the signal as being served by the extension arm 110. The system can be set up, for example, such that when a signal (e.g. a high signal) is received from the photodetector 506 indicating that the light from the LED 502 is being registered, image data is conveyed by the latching relay 306 to one computer, and when a signal (e.g. a low signal) is received from the photodetector 506 indicating that the light from the LED 502 is not being registered, image data is conveyed by the latching relay 306 to another computer.

In this way, the latching relay 306, based on the signal from the photodetector 506, can effect the flow of data transfer from the timer box 111 to either a first or a second USB interface (or other suitable) module in computer 112 or 114 as described above. The data transfer can be via a corresponding CAT5 cable or via another suitable type of interface, whether wired or wireless.

Thus, FIG. 5 shows an implementation of routing data from the x-ray source 106 to the appropriate operatory computer 112 or 114 in accordance with a preferred embodiment of the invention. The photodetector 506 may be, for example, a slotted optical switch, in particular OPB370 manufactured by TT electronics OPTEK Technology, or any other suitable type of photodetector.

Of course, this embodiment is not limited to using a latching relay driver. Other technologies and interfaces can be used instead to actuate data transfer to the appropriate dedicated computer. For example, the photodetector 506 can deliver the signal indicating the detected position to an Ethernet controller, which effects the flow of data transfer to an Ethernet or Internet Protocol (IP) address of the appropriate computer. Technologies such as Bluetooth or A02.11 networks also can be used.

Figure 6:
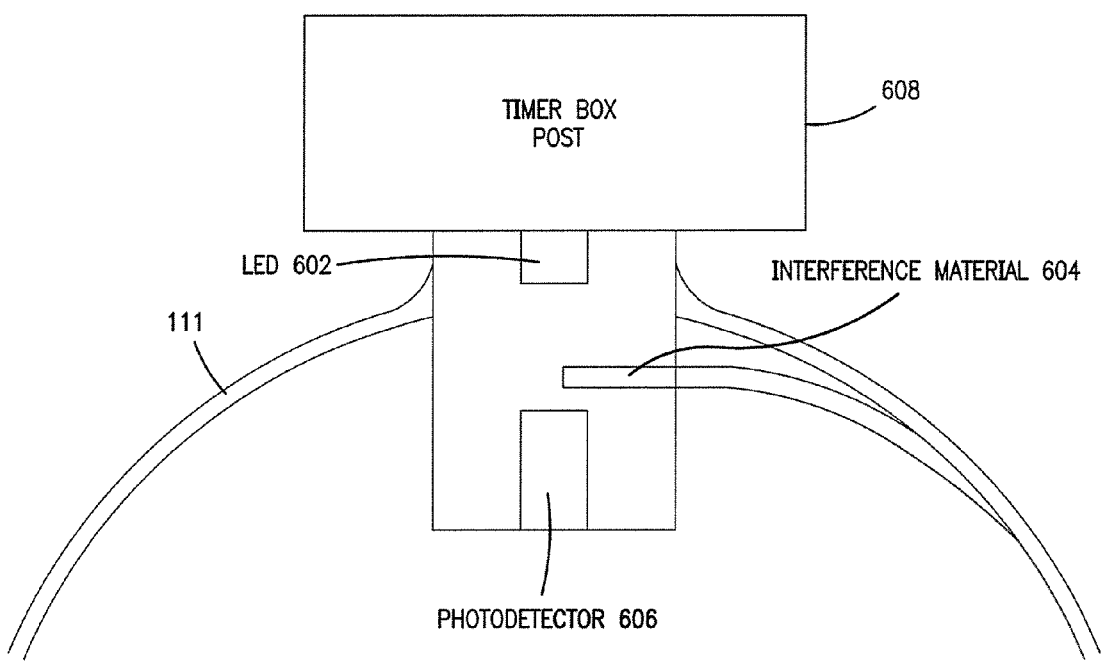
FIG. 6 shows another embodiment of the invention, in which orientation of the extension arm is detected using an electro-optic sensor.

FIG. 6 shows another exemplary embodiment of the invention, in which orientation of the extension arm is detected using an electro-optic sensor. It is noted that this embodiment can operate in conjunction with components similar to the cables 302, 304, latching relay driver 306, power supply 308, and standard timer board 312 shown in FIG. 3, although such components are not shown in FIG. 6 for simplicity sake.

In FIG. 6, an LED 602 is housed on (or otherwise coupled to), and rotates with, the timer box post 608. An interference material 604 is mounted to the timer box 111 and does not rotate. A photodetector 606 is preferably located on the timer box post 608, below the plane of the interference material 604, and rotates with the timer box post 608. The interference material 604 can be any suitable material that blocks light, for example plastic or metal, and can be of any suitable shape. It is of course to be understood that the interference material 604 is not limited to these examples. It is also to be understood that modifications may be made to the positioning of the LED 602, interference material 604, and photodetector 606; for example, the positions of the LED 602 and the photodetector 606 could be altered or swapped.

In the embodiment of FIG. 6, the LED 602 emits light which is registered by the photodetector 606 when the light is not being blocked by the interference material 604. Because the LED 602 and photodetector 606 move with rotation of the timer box post 608, which rotates as the extension arm 110 (not shown in FIG. 6) pivots, the interference material 604 will either block or not block the light depending on the position of the extension arm 110. In this way, the LED 602 emits light which is registered by the photodetector 606 when the extension arm 110 is in one operatory, and the light is not registered by the photodetector 606 when the extension arm 110 is in another operatory. The photodetector 606 sends a signal, for example a binary or other signal, depending on whether the light from the LED 602 is being registered, to a latching relay (e.g. 306) which actuates data transfer to the appropriate dedicated computer depending on which operatory is indicated by the signal as being served by the extension arm 110. The system can be set up, for example, such that when a signal (e.g. a high signal) is received from the photodetector 606 indicating that the light from the LED 602 is being registered, image data is conveyed by the latching relay 306 to one computer, and when a signal (e.g. a low signal) is received from the photodetector 606 indicating that the light from the LED 602 is not being registered, image data is conveyed by the latching relay 306 to another computer.

In this way, the latching relay 306, based on the signal from the photodetector 606, can effect the flow of data transfer from the timer box 111 to either a first or a second USB interface (or other suitable) module in computer 112 or 114 depending on the detected position, as described above. The data transfer can be via a corresponding CAT5 cable or via another suitable type of interface, whether wired or wireless.

Thus, FIG. 6 shows an implementation of routing data from the x-ray source 106 to the appropriate operatory computer 112 or 114 in accordance with another embodiment of the present invention. The photodetector 606 may be, for example, a slotted optical switch, in particular OPB370 manufactured by TT electronics OPTEK Technology, or any other suitable type of photodetector.

Of course, this embodiment is not limited to using a latching relay driver. Other technologies and interfaces could be used to actuate data transfer to the appropriate dedicated computer. For example, the photodetector 606 can deliver the signal indicating the detected position to an Ethernet controller, which effects the flow of data transfer to an Ethernet or Internet Protocol (IP) address of the appropriate computer. Technologies such as Bluetooth or A02.11 networks can be used.

Figure 7:
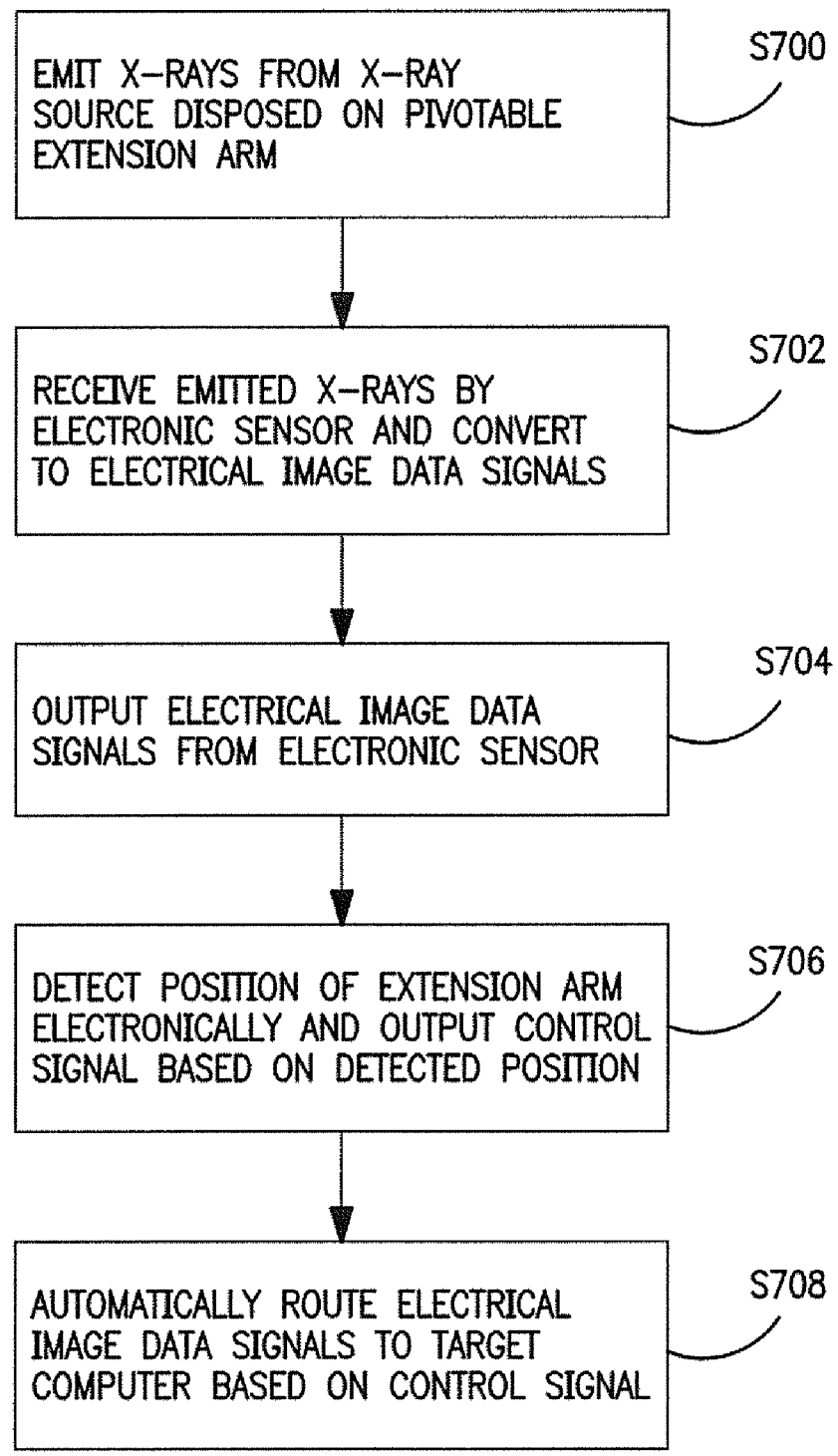
FIG. 7 is a flowchart showing a method, in accordance with one embodiment of the present invention, of automatically routing image data in a digital x-ray system to a target computer.

FIG. 7 is a flowchart showing a method, in accordance with one embodiment of the present invention, of automatically routing image data in a digital x-ray system (for example, 100 in FIG. 1) to a target computer of a plurality of dedicated computers 112, 114, each computer associated with a corresponding operatory 102, 104. The computers 112, 114 each perform a number of functions, including receiving and processing image data from a digital sensor, which may be wired or wireless.

In Step S700, x-rays are emitted from an x-ray source 106 disposed on an extension arm 110 which is capable of being pivoted or moved to allow the x-ray source 106 to be positioned to service a selected operatory 102, 104. The x-ray source 106 has an output that is directed towards an electronic sensor 108 which, in the dental scenario, is located in a patient's mouth behind the anatomy to be examined or elsewhere, depending on the applicable application of interest. In Step S702, the emitted x-rays are received by the electronic sensor 108 which converts the received x-rays to an electrical image data signal using any of a number of detector technologies, including CCD, CMOS-APS, and TFT, or another technology, depending on applicable system design criteria.

In Step S704 the electrical image data signal is outputted through a wired interface or towards a wireless interface (such as that shown in, for example, U.S. Patent Application Publication No. US 2005/0254625 A1, previously incorporated by reference herein). A wired interface operates to process the signal from a wired sensor 108, and also can perform such functions as driving the sensor 108, conditioning and formatting the signal into a more convenient format, and reading-out the signal. A wireless interface operates to process the signal from a wireless sensor 108, performing such functions including signal demodulation, for example. In either case, the processed image data signal is delivered from the interface to, for example, a memory (not shown) located in the control or timer box 111 through a suitable wired and/or wireless interface.

In Step S706, a position of the extension arm 110 is detected by using a method and device such as set forth herein (see description of FIGS. 3-6 above), or using another suitable technique. For example, a Hall effect switch 301, a micro-switch 401, a photodetector 506, 606, or another suitable type of detection device detects the position of the extension arm 110 in the above-described manner and outputs a control signal based on the detected position. In Step S708, the electrical image data signal obtained from the interface as described in Step S704 and (for example) stored in a memory (not shown) located in the timer box 111 is automatically routed from that memory to the target computer 112, 114 based on the control signal. Of course, the data may be routed without being stored in a memory. In any event, if Step S706 results in a determination that the arm 110 is positioned so as to service or otherwise be associated with operatory 102, then in Step S708 the control signal is indicative thereof and causes the electrical image data signal to be forwarded to computer 112. On the other hand, if Step S706 results in a determination that the arm 110 is positioned so as to service or otherwise be associated with operatory 104, then in Step S708 the control signal is indicative thereof and causes the electrical image data signal to be forwarded to computer 114. The target computer 112, 114 receives and processes the electrical image data signal, among other functions, and sends the created images to an output device such as a display for viewing, or a printer for printing.

The present invention is not limited to the above-described operatory configurations. As contemplated by the present invention, there may be two or more operatories. The operatories may be adjoining or adjacent to each other, or may be arranged in a circular or other working configuration in which one x-ray device is shared among all of the operatories. The x-ray device may be shared in a pass-through configuration, that is, a configuration in which each operatory is separated by a partition wall and the x-ray source is passed through an opening in the partition (or passed above the partition), or in another suitable type of configuration. The present invention is also not limited to being used in digital radiography systems, and of course can be used in any suitable application.

The present invention or any part(s) or function(s) thereof may be implemented using hardware, software or a combination thereof and may be implemented in one or more computer systems or other processing systems. It is noted that the various components of the present invention may be controlled by one or more modules coupled to the various components. The modules can operate in accordance with software control programs and operating routines stored in an associated memory or memories. The modules and their sub-modules can write and/or read information to/from the memory or memories.

In this way, modules can perform operations in accordance with the system, method, and apparatus of the present invention. The modules may be implemented using hardcoded computational modules or other types of circuitry, or a combination of software and circuitry modules. Software routines for performing the modules can, in one embodiment, be stored as instructions in a memory and can be executed by a processor of a control module.

In an embodiment where the invention is implemented using software, the software may be stored in a computer program product, a computer program medium, or a computer usable medium, and loaded into a computer system using a removable storage drive, a hard drive, or a communications interface. The control logic (software), when executed by a processor, causes the processor to perform the functions of the invention as described herein.

In this document, the terms "computer program medium" and "computer usable medium" are used to refer generally to media such as a removable storage drive, a hard disk installed in a hard disk drive, and signals. These computer program products provide software to the system.

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. Thus, the present invention should not be limited by any of the above described exemplary embodiments, but should be defined only in accordance with the following claims and their equivalents.

What is claimed is:

1. A method of operating a digital x-ray system having a plurality of information processors, each information processor associated with a corresponding one of a plurality of operatories, comprising the steps of:
   detecting at least one image in response to at least one energy source emitting energy, while the energy source is associated with an extension arm which is positioned to serve a selected one of the operatories, and outputting an electrical image data signal representing the detected image;
   detecting a position of the extension arm; and
   automatically routing the outputted electrical image data signal to the information processor associated with the selected operatory based on the detected position.

2. The method as set forth in claim 1, further comprising the step of transmitting a signal generated based on the detected position to an Ethernet controller which performs the routing step.

3. The method as set forth in claim 1, further comprising the step of transmitting a signal generated based on the detected position to a latching relay which performs the routing step.

4. The method as set forth in claim 1, further comprising the step of indicating the detected position to an operator.

5. The method as set forth in claim 1, wherein the step of detecting a position of the extension arm includes using a Hall effect switch.

6. The method as set forth in claim 1, wherein the step of detecting a position of the extension arm includes using a micro-switch.

7. A digital x-ray system having a plurality of information processors, each information processor associated with a corresponding one of a plurality of operatories, comprising:
   an electronic sensor adapted to detect at least one image in response to at least one energy source emitting energy, while the energy source is associated with an extension arm which is positioned to serve a selected one of the operatories, and adapted to output an electrical image data signal representing the detected image;
   a detector adapted to detect a position of the extension arm; and
   a controller adapted to automatically route the outputted electrical image data signal to the information processor associated with the selected operatory based on the detected position.

8. The system as set forth in claim 7, wherein the detector comprises a Hall effect switch.

9. The system as set forth in claim 7, wherein the detector comprises a micro-switch.

10. The system as set forth in claim 7, wherein the detector comprises a photodetector which detects light emitted from a user-perceptible interface based on a position of the extension arm.

11. The system as set forth in claim 10, wherein the user-perceptible interface comprises a plurality of LEDs.

12. The system as set forth in claim 10, further comprising an interference material which blocks the emitted light from being detected by the photodetector when the extension arm is in one position, and does not block the emitted light from being detected by the photodetector when the extension arm is in another position.

13. The system as set forth in claim 12, wherein the interference material comprises one of plastic and metal.

14. The system as set forth in claim 7, wherein the controller is an Ethernet controller.

15. The system as set forth in claim 7, wherein the controller is a latching relay.

16. The system as set forth in claim 7, further comprising a user-perceptible interface for indicating the detected position to an operator.

17. The system as set forth in claim 16, wherein the user-perceptible interface comprises a plurality of LEDs.

18. The system as set forth in claim 7, wherein the electronic sensor is a wireless sensor.

19. The system as set forth in claim 7, wherein the electronic sensor is a wired sensor.

20. A method comprising the steps of:
   detecting a position of an extension arm electronically; and
   communicating an electrical image data signal with one of a plurality of information processors based on the detected position, each of said information processors being capable of processing image data.

* * * * *